US00PP30649P2

(12) United States Plant Patent
Sapia

(10) Patent No.: US PP30,649 P2
(45) Date of Patent: Jul. 2, 2019

(54) ***HELICHRYSUM* PLANT NAMED 'HYBHS18538'**

(50) Latin Name: ***Helichrysum italicum* x *panormitanum***
Varietal Denomination: HYBHS18538

(71) Applicant: Flavio Sapia, Sanremo (IT)

(72) Inventor: Flavio Sapia, Sanremo (IT)

( * ) Notice: Subject to any disclaimer, the term of this patent is extended or adjusted under 35 U.S.C. 154(b) by 0 days.

(21) Appl. No.: 15/998,354

(22) Filed: Aug. 6, 2018

(51) Int. Cl.
*A01H 5/02* (2018.01)
*A01H 6/14* (2018.01)

(52) U.S. Cl.
USPC ..... Plt./359

(58) Field of Classification Search
USPC ..... Plt./263.1, 359
See application file for complete search history.

*Primary Examiner* — Susan McCormick Ewoldt
*Assistant Examiner* — Karen M Redden
(74) *Attorney, Agent, or Firm* — Barbara Campbell; Cochran Freund & Young LLC

(57) ABSTRACT

A new *Helichrysum* plant particularly distinguished by a plant having greyed-green leaves, a trailing habit and long stems, is disclosed.

1 Drawing Sheet

Genus and species: *Helichrysum italicum* x *panormitanum.*

Variety denomination: 'HYBHS18538'.

BACKGROUND OF THE NEW PLANT

The present invention comprises a new and distinct variety of *Helichrysum*, botanically known as *Helichrysum italicum* x *panormitanum*, and hereinafter referred to by the variety name 'HYBHS18538'. 'HYBHS18538' originated from a cross conducted in in May 2012 in Sanremo, Italy between an un-named and unpatented *Helichrysum italicum* female parent and an un-named and unpatented male *Helichrysum panormitanum* parent.

The seeds from the cross were sown and plants were grown outdoors for evaluation, where an individual plant designated 'HYBHS18538' was selected from the group of plants in February 2013. In June 2013 in Sanremo, Italy, 'HYBHS18538' was first vegetatively propagated by stem cuttings. 'HYBHS18538' was found to reproduce true to type in successive generations of asexual propagation via stem cuttings.

SUMMARY

The following are the most outstanding and distinguishing characteristics of this new variety when grown under normal horticultural practices in Sanremo, Italy and Stuttgart, Germany.

1. A plant having greyed-green leaves, a trailing habit; and
2. Long stems.

DESCRIPTION OF THE PHOTOGRAPH

This new *Helichrysum* plant is illustrated by the accompanying photograph which shows the plant's overall plant habit including form, and foliage. The photograph is of a 14-week-old plant grown in a greenhouse in a 10.5 cm pot in Stuttgart, Germany in February 2018. The colors shown are as true as can be reasonably obtained by conventional photographic procedures.

DESCRIPTION OF THE NEW VARIETY

The following detailed descriptions set forth the distinctive characteristics of 'HYBHS18538'. The data which define these characteristics were collected from in Stuttgart, Germany in May 2018 on 14-week-old plants grown in a 10.5 cm pot in a glass greenhouse with a pinch date one week after potting. Color references are to The R.H.S. Colour Chart of The Royal Horticultural Society of London (R.H.S.), 5$^{th}$ edition (2007).

Classification:
- *Family.*—Asteraceae.
- *Botanical.*—*Helichrysum italicum* x *panormitanum.*
- *Common.*—Italian strawflower.
- *Designation.*—'HYBHS18538'.

Parentage:
- *Female parent.*—An un-named and unpatented *Helichrysum italicum.*
- *Male parent.*—An un-named and unpatented *Helichrysum panormitanum.*

Plant:
- *Habit.*—Trailing.
- *Height.*—20.0 cm to 25.0 cm.
- *Spread.*—50.0 cm to 60.0 cm.
- *Life cycle.*—From February to October.
- *Time to produce a rooted cutting.*—3 to 4 weeks.
- *Root description.*—Fine, white to light brown, freely branching and dense.
- *Time to get a finished plant.*—8 weeks.
- *Propagation type.*—Vegetative stem cuttings.

Lateral branches:
- *Number of branches per plant.*—Depends on pinching, 6 to 8.
- *Color.*—RHS 155C (White).
- *Pubescence.*—Absent.
- *Stem form* (*in cross section*).—Round.

*Diameter.*—3.0 mm to 4.0 mm.
*Length.*—25.0 cm to 35.0 cm.
*Internode length.*—0.6 cm to 0.8 cm.
*Anthocyanin.*—Absent.

Leaves:
*Arrangement.*—Alternate.
*Length.*—3.5 cm to 6.5 cm.
*Width.*—2.5 mm to 3.0 mm.
*Shape.*—Ensiform.
*Apex.*—Subobtusus.
*Base.*—Auriculate.
*Margin.*—Entire.
*Surface texture (both upper and lower surfaces).*—Pubescent, hoary.
*Color, immature leaves.*—(Younger leaves) depends on climate conditions. Upper surface: RHS 189B (Greyed-green). Lower surface: RHS 189B (Greyed-green).
*Color, mature leaves.*—Older leaves (at the first centimeter of a branch). Upper surface: RHS 189A (Greyed-green). Lower surface: RHS 191A (Greyed-green).
*Venation pattern.*—Hyphodromous.
*Venation color.*—Upper surface: RHS 188D (Greyed-green). Lower surface: RHS 188D (Greyed-green).
*Petiole.*—Absent.

Flower and reproductive organs: Not observed to date.
Fruit and seed set: None observed.
Disease and pest/insect resistance: No disease and pest/insect resistance observed.

COMPARISON WITH PARENTAL LINES AND KNOWN VARIETY

'HYBHS18538' is distinguished from its parents as described in Table 1.

TABLE 1

Comparison with Parental Lines

| Characteristic | 'HYBHS18538' | Female Parent | Male Parent |
|---|---|---|---|
| Habit | Trailing | Upright | Upright |
| Stem appearance | Long | Short | Long |

'HYBHS18538' is most similar to the *Helichrysum italicum* 'Silbernadel' (unpatented). Differences between the varieties are described in Table 2.

TABLE 2

Comparison with Similar Variety

| Characteristic | 'HYBHS18538' | 'Silbernadel' |
|---|---|---|
| Habit | Trailing | Upright |

I claim:

1. A new and distinct variety of *Helichrysum* plant designated 'HYBHS18538' as illustrated and described herein.

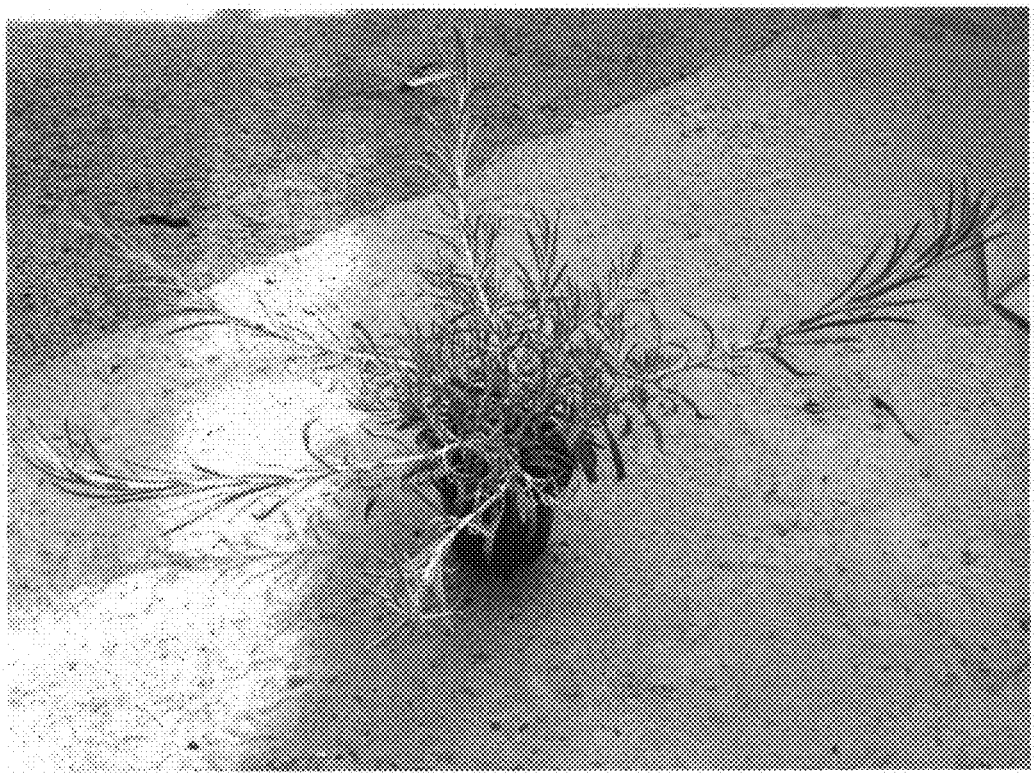

* * * * *